US010603268B2

(12) United States Patent
Plos et al.

(10) Patent No.: US 10,603,268 B2
(45) Date of Patent: *Mar. 31, 2020

(54) COMPOSITION COMPRISING A SILICONE FUNCTIONALIZED WITH AT LEAST ONE ALKOXYSILANE UNIT AND A NONIONIC OR ANIONIC FIXING POLYMER

(71) Applicant: L'OREAL, Paris (FR)

(72) Inventors: Gregory Plos, Paris (FR); Nicolas Daubresse, La Celle Saint Cloud (FR); Patrice Lerda, Asnieres (FR); Valerie Favreau, Mery-sur-Oise (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/547,138

(22) PCT Filed: Jan. 27, 2016

(86) PCT No.: PCT/EP2016/051697
§ 371 (c)(1),
(2) Date: Jul. 28, 2017

(87) PCT Pub. No.: WO2016/120322
PCT Pub. Date: Aug. 4, 2016

(65) Prior Publication Data
US 2018/0015024 A1 Jan. 18, 2018

(30) Foreign Application Priority Data

Jan. 29, 2015 (FR) ..................... 15 50690

(51) Int. Cl.
| A61K 8/898 | (2006.01) |
| A61K 8/81 | (2006.01) |
| A61Q 5/06 | (2006.01) |
| C08L 83/08 | (2006.01) |
| A61K 8/04 | (2006.01) |
| A61K 8/91 | (2006.01) |
| A61Q 5/04 | (2006.01) |
| C08L 33/26 | (2006.01) |
| C08G 77/26 | (2006.01) |
| C08G 77/28 | (2006.01) |

(52) U.S. Cl.
CPC .............. *A61K 8/898* (2013.01); *A61K 8/046* (2013.01); *A61K 8/8135* (2013.01); *A61K 8/8147* (2013.01); *A61K 8/8158* (2013.01); *A61K 8/8176* (2013.01); *A61K 8/8182* (2013.01); *A61K 8/91* (2013.01); *A61Q 5/04* (2013.01); *A61Q 5/06* (2013.01); *C08L 83/08* (2013.01); *A61K 2800/5422* (2013.01); *A61K 2800/5424* (2013.01); *C08G 77/26* (2013.01); *C08G 77/28* (2013.01); *C08L 33/26* (2013.01)

(58) Field of Classification Search
None
See application file for complete search history.

(56) References Cited

U.S. PATENT DOCUMENTS

| 2,047,398 A | 7/1936 | Voss et al. |
| 2,102,113 A | 12/1937 | Djordjevitch |
| 2,723,248 A | 11/1955 | Wright |
| 3,579,629 A | 5/1971 | Pasero et al. |
| 3,589,978 A | 6/1971 | Kamal et al. |
| 3,716,633 A | 2/1973 | Viout et al. |
| 3,810,977 A | 5/1974 | Levine et al. |
| 3,836,537 A | 9/1974 | Boerwinkle et al. |
| 3,910,862 A | 10/1975 | Barabas et al. |
| 3,925,542 A | 12/1975 | Viout et al. |
| 3,946,749 A | 3/1976 | Papantoniou |
| 3,966,403 A | 6/1976 | Papantoniou et al. |
| 3,966,404 A | 6/1976 | Papantoniou et al. |
| 3,990,459 A | 11/1976 | Papantoniou |
| 4,031,307 A | 6/1977 | DeMartino et al. |
| 4,128,631 A | 12/1978 | Lundmark et al. |
| 4,129,711 A | 12/1978 | Viout et al. |
| 4,131,576 A | 12/1978 | Iovine et al. |
| 4,137,208 A | 1/1979 | Elliott |
| 4,165,367 A | 8/1979 | Chakrabarti |
| 4,166,473 A | 9/1979 | Bauer et al. |
| 4,223,009 A | 9/1980 | Chakrabarti |
| 4,282,203 A | 8/1981 | Jacquet et al. |
| 4,289,752 A | 9/1981 | Mahieu et al. |
| 4,341,229 A | 7/1982 | Bauer et al. |
| 4,957,732 A | 9/1990 | Grollier et al. |
| 5,520,199 A | 5/1996 | Sturla |

(Continued)

FOREIGN PATENT DOCUMENTS

| DE | 2330956 A1 | 1/1974 |
| EP | 0080976 A1 | 6/1983 |

(Continued)

OTHER PUBLICATIONS

Notification of Reasons for Refusal for counterpart Japanese Application No. 2017-540121, dated Oct. 29, 2018.
International Search Report for PCT/EP2016/051697, dated Mar. 21, 2016.
International Search Report for PCT/EP2016/051696, dated Apr. 8 2016.
International Search Report for PCT/EP2016/051712, dated Mar. 23, 2016.
Todd, Charles, et al., "Volatile Silicone Fluids for Cosmetic Formulations," Cosmetics and Toiletries, vol. 91, Jan. 1976, pp. 29-32.
"Kosmeti sche Zusamrnensetzungen," IP.com Journal, IP.com, Inc., NY, XP013146799, Aug. 4, 2011.

(Continued)

*Primary Examiner* — Katherine Peebles
(74) *Attorney, Agent, or Firm* — The Marbury Law Group, PLLC

(57) ABSTRACT

The present invention relates to a hair composition comprising: (i) one or more polymers containing a silicone unit bearing alkoxy-(aminomethyl)-silyl functional groups; (ii) one or more nonionic fixing polymers and/or one or more anionic fixing polymers.

19 Claims, No Drawings

(56) References Cited

U.S. PATENT DOCUMENTS

| | | | |
|---|---|---|---|
| 5,520,200 A | 5/1996 | Sturla | |
| 5,679,324 A * | 10/1997 | Lisboa | A61K 8/046 424/45 |
| 8,217,113 B2 | 7/2012 | Scheim et al. | |
| 2006/0110351 A1 | 5/2006 | Koehler et al. | |
| 2007/0232729 A1 | 10/2007 | Briehn et al. | |
| 2010/0258141 A1 | 10/2010 | Paul et al. | |
| 2010/0307528 A1 | 12/2010 | Restle et al. | |
| 2012/0064018 A1 | 3/2012 | Schultze et al. | |
| 2013/0142750 A1 | 6/2013 | Fair et al. | |
| 2014/0161756 A1 | 6/2014 | Beer et al. | |
| 2014/0245542 A1 | 9/2014 | Schulze zur Wiesche et al. | |
| 2014/0271750 A1 | 9/2014 | Schulze zur Wiesche | |
| 2015/0104397 A1 | 4/2015 | Small et al. | |

FOREIGN PATENT DOCUMENTS

| | | |
|---|---|---|
| EP | 0186507 A2 | 7/1986 |
| EP | 0342834 A2 | 11/1989 |
| EP | 0659393 A1 | 6/1995 |
| EP | 0662314 A1 | 7/1995 |
| FR | 1222944 A | 6/1960 |
| FR | 1400366 A | 5/1965 |
| FR | 1564110 A | 4/1969 |
| FR | 1580545 A | 9/1969 |
| FR | 2077143 A | 10/1971 |
| FR | 2198719 A1 | 4/1974 |
| FR | 2265781 A1 | 10/1975 |
| FR | 2265782 A1 | 10/1975 |
| FR | 2273492 A1 | 1/1976 |
| FR | 2350384 A1 | 12/1977 |
| FR | 2357241 A2 | 2/1978 |
| FR | 2393573 A1 | 1/1979 |
| FR | 2439798 A1 | 5/1980 |
| FR | 2990131 A1 | 11/2013 |
| FR | 3008888 A1 | 1/2015 |
| GB | 839805 A | 6/1960 |
| GB | 922457 A | 4/1963 |
| GB | 1021400 A | 3/1966 |
| GB | 1408388 A | 10/1975 |
| GB | 1572626 A | 7/1980 |
| JP | H08-24036 A | 1/1996 |
| JP | H08-24037 A | 1/1996 |
| JP | 2006-249002 A | 9/2006 |
| JP | 2010-241812 A | 10/2010 |
| JP | 2010-540137 A | 12/2010 |
| JP | 2012-516313 A | 7/2012 |
| JP | 2014-523447 A | 9/2014 |
| JP | 2015-500280 A | 1/2015 |
| LU | 75370 A1 | 2/1978 |
| LU | 75371 A1 | 2/1978 |
| WO | 2005/108495 A2 | 11/2005 |
| WO | 2009/019165 A1 | 2/2009 |
| WO | WO 2013/014140 * | 1/2013 |
| WO | WO 2014/151667 * | 9/2014 |
| WO | 2015/011258 A1 | 1/2015 |
| WO | 2016/120321 A1 | 8/2016 |
| WO | 2016/120334 A1 | 8/2016 |

OTHER PUBLICATIONS

"Table 31; Hair Fixative Polymers Commonly Used in Hair Spray Products ED—Dekker," Hair and Hair Care (Cosmetic Science and Technology)—Series Title: Cosmetic Science and Technology Series, vol. 17, XP007923230, Jan. 1, 1997, pp. 136-137.

Non-Final Office Action for copending U.S. Appl. No. 15/547,166, dated Jan. 31, 2019.

Non-Final Office Action for copending U.S. Appl. No. 15/547,142, dated Nov. 19, 2018.

Final Office Action for co-pending U.S. Appl. No. 15/547,166, dated Sep. 20, 2019.

Notice of Allowance for co-pending U.S. Appl. No. 15/547,142, dated Jul. 12, 2019.

* cited by examiner

COMPOSITION COMPRISING A SILICONE FUNCTIONALIZED WITH AT LEAST ONE ALKOXYSILANE UNIT AND A NONIONIC OR ANIONIC FIXING POLYMER

CROSS REFERENCE TO RELATED APPLICATIONS

This is a national stage application of PCT/EP2016/051697, filed internationally on Jan. 27, 2016, which claims priority to French Application No. 1550690, filed on Jan. 29, 2015, both of which are incorporated by reference herein in their entireties.

The present invention relates to a hair composition comprising one or more particular silicones and one or more nonionic and/or anionic fixing polymers. The present invention also relates to a process for shaping and/or holding the hairstyle using said composition.

In the field of hairstyling, in particular among products intended for shaping and/or holding the hairstyle, the hair compositions that are the most widespread on the cosmetics market are compositions consistuted essentially of a solution, which is usually alcoholic or aqueous-alcoholic, and of one or more polymers, known as fixing polymers, which are generally film-forming polymers. These polymers thus have the function of making welds between the hairs so as to be able to structure the hairstyle and give it long-lasting hold.

However, certain fixing polymers result in hardening of the head of hair. This drawback leads to a set hairstyle and to disentangling that is often difficult at the end of the day, the hair having a dry feel.

To improve the cosmetic feel of the hair, it is known practice to add silicone or oxyethylene compounds. However, this type of combination has a tendency to reduce the level of fixing of the compositions and to reduce the hairstyle hold.

However, these products are not entirely satisfactory, especially in terms of the balance between the fixing power and the cosmetic qualities of the head of hair, and especially the feel of the hair during drying, immediately after application and after removal by brushing. Either a very high level of fixing is obtained with a product which appears as tacky during drying, and then rigid, dry, or even coarse. Or a feel is obtained that remains relatively natural, but with a low level of fixing.

There is thus a real need to find compositions, especially for hairstyling, which allow a good level of fixing and long-lasting hairstyle hold while at the same time giving the hair a cosmetic feel.

The Applicant has found, surprisingly and unexpectedly, that the combination of one or more polymers containing a silicone unit bearing alkoxy-(aminomethyl)-silyl functional groups and one or more nonionic and/or anionic fixing polymers makes it possible to obtain a head of hair that does not have the above drawbacks.

Specifically, this combination makes it possible to obtain strong fixing of the head of hair, which lasts throughout the day, while at the same time giving the hair a cosmetic feel. The hair is held in the desired shape without being set or hardened by the composition, the hair being soft, supple and smooth.

The subject of the invention is thus a hair composition comprising:
(i) one or more polymers containing a silicone unit bearing alkoxy-(aminomethyl)-silyl functional groups;
(ii) one or more nonionic fixing polymers and/or one or more anionic fixing polymers.

Another subject of the present invention consists of an aerosol device which comprises a container containing a hair composition comprising (i) one or more polymers containing a silicone unit bearing alkoxy-(aminomethyl)-silyl functional groups; (ii) one or more nonionic fixing polymers and/or one or more anionic fixing polymers, and a propellant gas.

Another subject of the present invention consists of a process for shaping and/or holding the hairstyle in which is applied a hair composition, comprising:
(i) one or more polymers containing a silicone unit bearing alkoxy-(aminomethyl)-silyl functional groups;
(ii) one or more nonionic fixing polymers and/or one or more anionic fixing polymers.

Other subjects, characteristics, aspects and advantages of the invention will emerge even more clearly on reading the description and the example that follows.

The composition of the invention comprises one or more polymers containing a silicone unit bearing alkoxy-(aminomethyl)-silyl functional groups.

The polymer(s) containing a silicone unit bearing alkoxy-(aminomethyl)-silyl functional groups are preferably of formula (I) below:

$$Z_2-\underset{\underset{Z_3}{|}}{\overset{\overset{O-R_1}{|}}{Si}}-O-\underset{\underset{R_b}{|}}{\overset{\overset{R_a}{|}}{Si}}-\left[O-\underset{\underset{R_b}{|}}{\overset{\overset{R_a}{|}}{Si}}\right]_n-O-\underset{\underset{Z_3}{|}}{\overset{\overset{R_1-O}{|}}{Si}}-Z_2 \qquad (I)$$

in which:
$Z_2$ represents a group $-CH_2-NR_3R_4$;
$Z_3$ represents a group $OR_5$ or $R_6$;
$R_1$ represents a $C_1$-$C_6$ alkyl group,
$R_3$ represents a hydrogen atom or a group $R_7$; $R_4$ represents a $C_1$-$C_6$ alkyl group or a $C_5$-$C_6$ cycloalkyl group; or
$R_3$ and $R_4$ may form, with the nitrogen atom that bears them, a 5- to 8-membered heterocycle comprising from 1 to 3 heteroatoms,
$R_5$, $R_6$ and $R_7$, which may be identical or different, represent a $C_1$-$C_6$ alkyl group, and
$R_a$ and $R_b$, which may be identical or different, represent a $C_1$-$C_2$ alkyl group,
n represents an integer greater than 1.

Preferably, the $C_1$-$C_6$ alkyl groups are methyl or ethyl groups.

Preferably, $R_1$ is an ethyl group.

When $R_4$ represents a $C_5$-$C_6$ cycloalkyl group, it preferably represents a $C_6$ cycloalkyl group such as cyclohexyl.

Preferably, n ranges from 1 to 10000, preferably from 5 to 1000 and more preferably from 8 to 400.

According to a particular embodiment of the invention, $Z_2$ represents a group $-CH_2-NR_3R_4$, $R_4$ represents an alkyl group, preferably a cyclohexyl, $R_3$ represents a hydrogen atom and $R_5$ represents an ethyl group.

According to a preferred embodiment of the invention, $R_3$ and $R_4$ form, with the nitrogen atom that bears them, a 5- to 8-membered heterocycle comprising from 1 to 3 heteroatoms. Again preferably, $R_3$ and $R_4$ form, with the nitrogen that bears them, a cyclic group, preferably morpholino, and $R_5$ represents an ethyl group.

Preferably, in formula (I), $SiR_aR_b-[OSiR_aR_b]n-$ is a unit derived from a linear silicone with a weight-average molecular mass (Mw) ranging from 200 to 40000 and more preferentially from 400 to 25000 g/mol.

As examples of polymers that may be used according to the invention, mention will be made of:

Polymers of Formula (Ia)

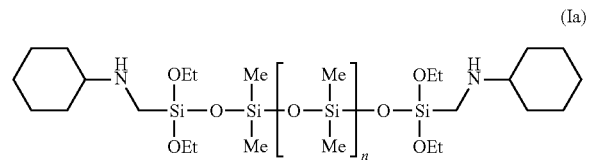

(Ia)

The polymers of formula (Ia) may be obtained by reacting a silicone bearing hydroxyl end groups with triethoxycyclohexylaminomethylsilane especially according to the techniques described in WO 2005/108 495.

According to a particular example, polymer (Iaa), corresponding to formula (Ia), is obtained according to the operating scheme presented above, starting with a silicone with a weight-average molecular mass Mw of 4750 g/mol.

Polymers of Formula (Ib)

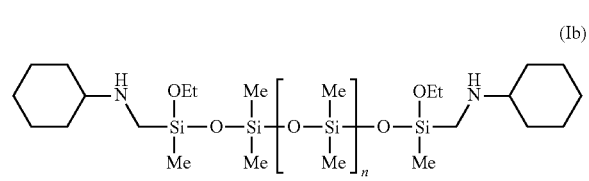

(Ib)

The polymers of formula (Ib) may be obtained by reacting a silicone bearing hydroxyl end groups with diethoxycyclohexylaminomethylmethylsilane especially according to the techniques described in WO 2005/108 495.

According to a particular example, polymer (Iba), corresponding to formula (Ib), is obtained according to the operating scheme presented above, starting with a silicone with a weight-average molecular mass Mw of 4750 g/mol.

Polymers of Formula (Ic)

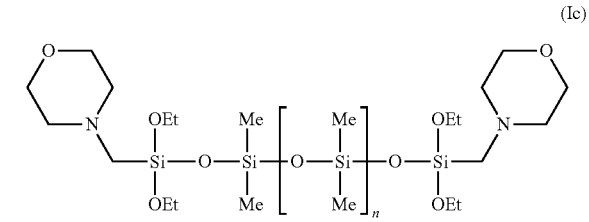

(Ic)

The polymers of formula (Ic) may be obtained by reacting a silicone bearing hydroxyl end groups with triethoxymorpholinomethylsilane especially according to the techniques described in WO 2009/019 165.

According to a particular example, polymer (Ica), corresponding to formula (Ic), is obtained according to the operating scheme presented above, starting with a silicone with a weight-average molecular mass Mw of 4750 g/mol.

According to another particular example, polymer (Icb), corresponding to formula (Ic), is obtained according to the operating scheme presented above, starting with a silicone with a weight-average molecular mass of 10600 g/mol.

According to another particular example, polymer (Icc), corresponding to formula (Ic), is obtained according to the operating scheme presented above, starting with a silicone with a weight-average molecular mass of 14600 g/mol.

According to another particular example, polymer (Icd), corresponding to formula (Ic), is obtained according to the operating scheme presented above, starting with a silicone with a weight-average molecular mass Mw of 21100 g/mol.

According to another particular example, polymer (Ice), corresponding to formula (Ic), is obtained according to the operating scheme presented above, starting with a silicone with a weight-average molecular mass Mw of 550 g/mol.

According to another particular example, polymer (Icf), corresponding to formula (Ic), is obtained according to the operating scheme presented above, starting with a silicone with a weight-average molecular mass Mw of 1000 g/mol.

According to another particular example, polymer (Icg), corresponding to formula (Ic), is obtained according to the operating scheme presented above, starting with a silicone with a weight-average molecular mass Mw of 1200 g/mol.

According to another particular example, polymer (Ich), corresponding to formula (Ic), is obtained according to the operating scheme presented above, starting with a silicone with a weight-average molecular mass Mw of 1700 g/mol.

Polymers of Formula (Id)

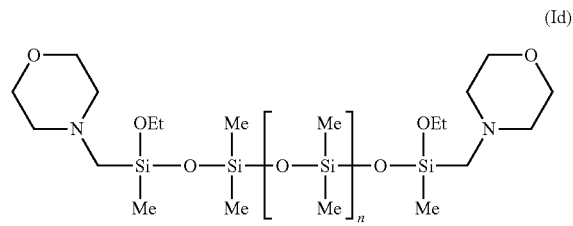

(Id)

The polymers of formula (Id) may be obtained by reacting a silicone bearing hydroxyl end groups with diethoxymorpholinomethylmethylsilane especially according to the techniques described in document WO 2009/019 165.

According to a particular example, the polymer of formula (Ida), corresponding to formula (Id), is obtained according to the operating scheme presented above, starting with a silicone with a weight-average molecular mass Mw of 4750 g/mol.

According to another particular example, the polymer of formula (Idb), corresponding to formula (Id), is obtained according to the operating scheme presented above, starting with a silicone with a weight-average molecular mass Mw of 10600 g/mol.

According to another particular example, the polymer of formula (Idc), corresponding to formula (Id), is obtained according to the operating scheme presented above, starting with a silicone with a weight-average molecular mass Mw of 14600 g/mol.

According to another particular example, the polymer of formula (Idd), corresponding to formula (Id), is obtained according to the operating scheme presented above, starting with a silicone with a weight-average molecular mass Mw of 21100 g/mol.

The content of the polymer(s) containing a silicone unit bearing alkoxy-(aminomethyl)-silyl functional groups, preferably of formula (I), in the composition containing them generally ranges from 0.1% to 40% by weight, preferably from 0.5% to 30% by weight and more particularly from 1% to 10% by weight relative to the total weight of the composition in which they are used.

The composition of the invention also comprises one or more anionic fixing polymers and/or one or more nonionic fixing polymers.

For the purposes of the invention, the term "fixing polymer" means any polymer that is capable, by application to the hair, of giving a shape to a head of hair or of holding the hair in an already acquired shape.

Anionic fixing polymers that may be mentioned include polymers containing groups derived from carboxylic, sulfonic or phosphoric acids, and having a number-average molecular mass of between 500 and 5000000.

The carboxylic groups are provided by unsaturated monocarboxylic or dicarboxylic acid monomers, such as those corresponding to the formula:

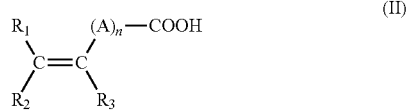

in which n is an integer from 0 to 10, A denotes a methylene group which is optionally connected to the carbon atom of the unsaturated group or to the neighbouring methylene group when n is greater than 1, via a heteroatom such as oxygen or sulfur, $R_1$ denotes a hydrogen atom or a phenyl or benzyl group, $R_2$ denotes a hydrogen atom, an alkyl group containing from 1 to 4 carbon atoms, or a carboxyl group, $R_3$ denotes a hydrogen atom, an alkyl group containing from 1 to 4 carbon atoms, or a —$CH_2$—COOH, phenyl or benzyl group.

In the formula (II) above, the alkyl group comprising from 1 to 4 carbon atoms may in particular denote methyl and ethyl groups.

The anionic fixing polymers containing carboxylic or sulfonic groups that are preferred are:

A) copolymers of acrylic or methacrylic acid or salts thereof, including copolymers of acrylic acid and acrylamide, and methacrylic acid/acrylic acid/ethyl acrylate/methyl methacrylate copolymers, more particularly Amerhold DR 25 sold by the company Amerchol, and sodium salts of polyhydroxycarboxylic acids. Mention may also be made of methacrylic acid/ethyl acrylate copolymers, in particular in aqueous dispersion, such as Luviflex Soft and Luvimer MAE, which are sold by the company BASF. Mention may also be made of the AMP-acrylate/$C_1$-$C_{18}$ alkylacrylate/$C_1$-$C_8$ alkylacrylamide/hydroxyethyl acrylate copolymers sold by the company GOO Chemical under the commercial reference Plascize® L-9700 or Plascize® L-9700U.

B) copolymers of acrylic or methacrylic acids with a monoethylenic monomer such as ethylene, styrene, vinyl esters, acrylic or methacrylic acid esters, which are optionally grafted on a polyalkylene glycol such as polyethylene glycol, and are optionally crosslinked. Such polymers are described in particular in French patent 1 222 944 and German patent application No. 2 330 956, the copolymers of this type comprising an optionally N-alkylated and/or hydroxyalkylated acrylamide unit in their chain as described especially in Luxembourg patent applications 75370 and 75371. Mention may also be made of copolymers of acrylic acid and $C_1$-$C_4$ alkyl methacrylate.

As another anionic fixing polymer from this class, mention may also be made of the branched anionic butyl acrylate/acrylic acid/methacrylic acid block polymer sold under the name Fixate G-100 L by the company Lubrizol (INCI name AMP-Acrylates/Allyl Methacrylate Copolymer).

C) copolymers derived from crotonic acid, such as those comprising, in their chain, vinyl propionate or acetate units, and optionally other monomers such as allyl or methallyl esters, vinyl ethers or vinyl esters of a linear or branched, saturated carboxylic acid with a long hydrocarbon-based chain, such as those comprising at least 5 carbon atoms, it being possible for these polymers optionally to be grafted and crosslinked, or else a vinyl, allyl or methallyl ester of an α- or (β-cyclic carboxylic acid. Such polymers are described, inter alia, in French patents Nos. 1 222 944, 1 580 545, 2 265 782, 2 265 781, 1 564 110 and 2 439 798. Commercial products that fall within this category are the resins 28-29-30, 26-13-14 and 28-13-10 sold by the company National Starch.

Mention may also be made, as copolymer derived from crotonic acid, of crotonic acid/vinyl acetate/vinyl tert-butyl-benzoate terpolymers, and in particular Mexomer PW supplied by the company Chimex.

D) polymers derived from maleic, fumaric or itaconic acids or anhydrides with vinyl esters, vinyl ethers, vinyl halides, phenylvinyl derivatives, acrylic acid and its esters; these polymers may be esterified. Such polymers are described in particular in U.S. Pat. Nos. 2,047,398, 2,723, 248 and 2,102,113 and GB patent 839 805, and especially those sold under the names Gantrez® AN or ES by the company ISP.

Polymers also falling into this category are the copolymers of maleic, citraconic or itaconic anhydrides and of an allyl or methallyl ester optionally comprising an acrylamide or methacrylamide group, an α-olefin, acrylic or methacrylic esters, acrylic or methacrylic acids or vinylpyrrolidone in their chain, the anhydride functions being monoesterified or monoamidated. These polymers are described, for example, in French patents 2 350 384 and 2 357 241 by the applicant.

E) polyacrylamides comprising carboxylate groups.

F) polymers comprising sulfonic groups. These polymers may be polymers comprising vinylsulfonic, styrenesulfonic, naphthalenesulfonic, acrylamidoalkylsulfonic or sulfoisophthalate units.

These polymers may in particular be chosen from:
polyvinylsulfonic acid salts having a molecular mass of between approximately 1000 and 100000, and also copolymers with an unsaturated comonomer, such as acrylic or methacrylic acids and esters thereof, and also acrylamide or derivatives thereof, vinyl ethers and vinylpyrrolidone;
polystyrenesulfonic acid salts and sodium salts, having a molecular mass of approximately 500000 and of about 100000. These compounds are described in patent FR 2 198 719;
polyacrylamidesulfonic acid salts such as those mentioned in U.S. Pat. No. 4,128,631;

G) grafted anionic silicone polymers;

The grafted silicone polymers used are preferably chosen from polymers containing a non-silicone organic backbone grafted with monomers containing a polysiloxane, polymers containing a polysiloxane backbone grafted with non-silicone organic monomers, and mixtures thereof.

H) Anionic polyurethanes, possibly comprising silicone grafts and silicones containing hydrocarbon-based grafts.

Examples of fixing polyurethanes that may especially be mentioned include the dimethylolpropionic acid/isophorone diisocyanate/neopentyl glycol/polyester diols copolymer (also known under the name polyurethane-1, INCI name)

sold under the brand name Luviset® PUR by the company BASF, and the dimethylolpropionic acid/isophorone diisocyanate/neopentyl glycol/polyester diols/silicone diamine copolymer (also known under the name polyurethane-6, INCI name) sold under the brand name Luviset® Si PUR A by the company BASF.

Another anionic polyurethane that may also be used is Avalure UR 450.

It is also possible to use polymers containing sulfoisophthalate groups, such as the polymers AQ55 and AQ48 sold by the company Eastman.

According to the invention, the anionic polymers are preferably selected from acrylic acid copolymers such as the acrylic acid/ethyl acrylate/N-tert-butylacrylamide terpolymer sold under the name Ultrahold Strong® by the company BASF, and methacrylic acid copolymers such as methacrylic acid/ethyl acrylate copolymers, especially in aqueous dispersion, such as Luviflex Soft and Luvimer MAE, which are sold by the company BASF, copolymers derived from crotonic acid such as vinyl acetate/vinyl tert-butylbenzoate/crotonic acid terpolymers and crotonic acid/vinyl acetate/vinyl neododecanoate terpolymers, which are sold under the name Resyn 28-2930 by the company AkzoNobel, polymers derived from maleic, fumaric or itaconic acids or anhydrides with vinyl esters, vinyl ethers, vinyl halides, phenylvinyl derivatives, acrylic acid and its esters, such as the monoesterified maleic anhydride/methyl vinyl ether copolymer sold under the name Gantrez® ES 425 by the company ISP, Luviset Si PUR, Mexomere PW, elastomeric or non-elastomeric anionic polyurethanes, and polymers containing sulfoisophthalate groups.

Even more preferentially, the anionic fixing polymer(s) are chosen from acrylic or methacrylic acid copolymers or salts thereof, and crotonic acid copolymers.

The nonionic fixing polymers that may be used according to the present invention are chosen, for example, from:
 polyalkyloxazolines,
 vinyl acetate homopolymers,
 vinyl acetate copolymers, for instance copolymers of vinyl acetate and of acrylic ester, copolymers of vinyl acetate and of ethylene, or copolymers of vinyl acetate and of maleic ester, for example of dibutyl maleate,
 acrylic ester homopolymers and copolymers, for instance copolymers of alkyl acrylates and of alkyl methacrylates, such as the products provided by the company Röhm & Haas under the names Primal® AC-261 K and Eudragit® NE 30 D, by the company BASF under the name 8845, or by the company Hoechst under the name Appretan® N9212,
 copolymers of acrylonitrile and of a nonionic monomer chosen, for example, from butadiene and alkyl (meth)acrylates, such as the products provided under the name CJ 0601 B by the company Röhm & Haas,
 styrene homopolymers,
 styrene copolymers, for instance copolymers of styrene and of alkyl (meth)acrylate, such as the products Mowilith® LDM 6911, Mowilith® DM 611 and Mowilith® LDM 6070 provided by the company Hoechst, the products Rhodopas® SD 215 and Rhodopas® DS 910 provided by the company Rhône-Poulenc, copolymers of styrene, of alkyl methacrylate and of alkyl acrylate, copolymers of styrene and of butadiene, or copolymers of styrene, of butadiene and of vinylpyridine,
 polyamides,
 vinyllactam homopolymers such as vinylpyrrolidone homopolymers and the polyvinylcaprolactam sold under the name Luviskol® Plus by the company BASF,
 vinyllactam copolymers, such as a poly(vinylpyrrolidone/vinyllactam) copolymer sold under the trade name Luvitec® VPC 55K65W by the company BASF, poly(vinylpyrrolidone/vinyl acetate) copolymers, such as those sold under the name PVPVA® S630L by the company ISP, Luviskol® VA 73, VA 64, VA 55, VA 37 and VA 28 by the company BASF and poly(vinylpyrrolidone/vinyl acetate/vinyl propionate) terpolymers, for instance the product sold under the name Luviskol® VAP 343 by the company BASF, and
 poly(vinyl alcohols).

The alkyl groups of the nonionic polymers mentioned above preferably contain from 1 to 6 carbon atoms.

Preferably, the nonionic fixing polymer(s) are chosen from vinyllactam homopolymers and vinyllactam copolymers.

Preferably, the composition comprises at least one anionic fixing polymer.

The nonionic fixing polymer(s) and/or one or more anionic fixing polymers are preferably present in an amount ranging from 0.1% to 20% by weight, preferably from 0.5% to 15% by weight and better still from 1% to 10% relative to the total weight of the composition in which they are used.

The composition according to the invention may also comprise one or more catalysts for catalysing the hydrolysis-condensation reactions of the alkoxysilane functions of the polymer containing a silicone unit bearing alkoxy-(aminomethyl)-silyl functional groups.

The catalyst may be chosen from acids and bases.

The acid may be chosen from mineral acids and organic acids.

The acid may be chosen in particular from lactic acid, acetic acid, citric acid, tartaric acid, hydrochloric acid, sulfuric acid and phosphoric acid, preferably hydrochloric acid.

The base may be chosen from mineral bases and organic bases.

The base may be chosen from ammonia and sodium hydroxide.

According to a particular embodiment, it is possible for the catalyst not to the present in the composition and to be mixed at the time of use with the composition comprising the polymer(s) containing a silicone unit bearing alkoxy-(aminomethyl)-silyl functional groups, or alternatively to be applied sequentially to the hair before or after the composition comprising the polymer(s) containing a silicone unit bearing alkoxy-(aminomethyl)-silyl functional groups.

The catalyst(s) may represent from 0.0001% to 10% by weight, preferably from 0.001% to 5% by weight and more particularly from 0.01% to 2% by weight relative to the total weight of the composition containing them.

The composition may be aqueous or anhydrous. When it contains any, the composition preferably contains less than 5% by weight of water relative to the total weight of the composition.

The composition is preferably anhydrous. For the purposes of the present invention, the term "anhydrous composition" means a composition having a water content of less than 3% by weight, preferably less than 2% by weight relative to the total weight of the composition, and/or a composition which does not contain any added water, i.e. the water that may be present in the composition according to the invention is more particularly bound water, such as the water of crystallization of salts, or traces of water absorbed by the starting materials used in the production of the compositions.

The composition(s) according to the invention may comprise one or more organic solvents, preferably chosen from alcohols, alkanes, esters and silicones, and mixtures thereof.

The alcohols are linear or branched $C_1$-$C_6$ monoalcohols or polyols.

The esters may be natural or synthetic.

The esters may be chosen especially from plant oils and esters of fatty acids or of fatty alcohols, such as isopropyl myristate.

The alkanes may be chosen especially from linear or branched $C_6$-$C_{15}$ alkanes and liquid paraffins.

The silicones may be chosen especially from cyclic silicones comprising from 4 to 6 silicon atoms and linear polydimethylsiloxanes.

Preferably, the organic solvent is chosen from ethanol, propanol, isopropanol, glycerol, undecane, tridecane, isododecane, isopropyl myristate, ethyl adipate, ethyl acetate, linear low-molecular-weight silicones or cyclic silicones such as cyclopentasiloxane, and also mixtures thereof.

According to a preferred embodiment, the solvent is chosen from ethanol and isopropanol, and mixtures thereof.

The organic solvents that may be used in the composition of the invention are liquids that preferably have a viscosity at 25° C. and at atmospheric pressure of less than or equal to 100 cSt.

When they are present, the organic solvent(s) may represent from 10% to 99.8%, preferably from 30% to 98% by weight and better still from 35% to 95% by weight relative to the total weight of the composition containing them.

The composition according to the invention may also contain one or more additives chosen from plasticizers, surfactants, and in particular nonionic and/or phosphate-based surfactants, silicones, fatty esters, fatty alcohols, anionic or nonionic polymers other than the fixing polymers, cationic, amphoteric or zwitterionic polymers, fragrances, dyes, UV-protective screening agents, acids, bases, nacres and glitter flakes.

These additives may be present in the composition according to the invention in an amount ranging from 0 to 20% by weight, relative to the total weight of the composition, when the propellant(s) are present in the composition.

A person skilled in the art will take care to select these optional additives and the amounts thereof so that they do not harm the properties of the compositions of the present invention.

The composition may be in the form of a solution, a dispersion or an emulsion. The polymer containing a silicone unit bearing alkoxy-(aminomethyl)-silyl functional groups may be emulsified as an oil-in-water or water-in-oil emulsion or as a multiple emulsion.

The composition according to the invention may be, inter alia, in the form of liquids that are more or less thickened, gels, creams, pastes or foams.

The composition in accordance with the invention may be packaged, for example, in a jar, in a tube, in a pump-action bottle, in a foamer or in an aerosol device that is common in cosmetics.

The composition according to the invention may, when it is intended to be packaged in an aerosol device, contain one or more propellants.

Examples of propellants that may be used in the composition of the present invention are liquefied gases such as dimethyl ether, chlorinated and/or fluorinated hydrocarbons such as 1,1-difluoroethane, or volatile hydrocarbons such as, in particular, $C_3$-$C_5$ alkanes, for instance propane, isopropane, n-butane, isobutane or pentane, or compressed gases such as air, nitrogen, carbon dioxide, and mixtures thereof.

Mention may be made preferentially of dimethyl ether, compressed air and $C_{3-5}$ alkanes and in particular propane, n-butane and isobutane, and mixtures thereof.

The propellant(s) may be present in the composition or, as a variant, in the container containing the composition, but separate from the composition.

The propellant(s) are preferably present in the composition.

When the propellant(s) are present in the composition, they are preferably present in an amount ranging from 2% to 90% by weight relative to the total weight of the composition.

In particular, when the composition is dispensed in aerosol spray form, it comprises a propellant gas in a content preferably ranging from 10% to 90% by weight, better still from 15% to 80% by weight and even more preferentially from 20% to 75% relative to the total weight of said composition.

When the composition is dispensed in aerosol foam form, it comprises a propellant gas in a content preferably ranging from 2% to 10% by weight relative to the total weight of said composition.

In the case of aerosol foams, the composition introduced into the aerosol device may, for example, be in the form of a lotion, or dispersions or emulsions which, after dispensing from the aerosol device, form foams to be applied to keratin materials.

These foams are preferably sufficiently stable not to rapidly liquefy and preferably must also rapidly disappear, either spontaneously or during the massaging which serves to make the composition penetrate into keratin materials and/or to distribute the composition over keratin materials and more particularly the head of hair and/or the hair.

In the case of aerosol foams, the composition may also contain at least one cationic, nonionic, anionic or amphoteric surfactant.

Preferably, the composition is dispensed in aerosol spray form, the composition then being in the form of a lacquer.

The invention also relates to an aerosol device which comprises a container containing a hair composition described previously and a propellant.

As already mentioned previously, the container contains both the propellant(s) and the other ingredients of the composition, in a single compartment, or as a variant in two compartments. According to the latter variant, the container may be constituted of an outer aerosol can comprising an inner bag hermetically welded to a valve. The various ingredients of the composition are introduced into the inner bag and a propellant is introduced between the bag and the can at a sufficient pressure to make the product come out in the form of a spray.

The container is equipped at its top end with a valve that seals the system.

Onto this valve is fitted a dispensing means, on which the user can press to make the product come out. This dispensing means is also known as a diffuser. It may comprise a single spray orifice, for example with a direct or turbulent-channel outlet. As a variant, it may comprise several spray orifices.

The invention also relates to a process for shaping and/or holding the hairstyle, which consists in applying to the hair the hair composition described previously by means of the device that has just been described.

According to a particular embodiment, the application may be performed in a single stage. In this case, a composition including one or more polymers containing a silicone unit bearing alkoxy-(aminomethyl)-silyl functional groups, preferably of formula (I), one or more nonionic fixing polymers and/or one or more anionic fixing polymers, and optionally one or more catalysts as defined previously, will be applied by spraying.

In this one-stage embodiment, the composition sprayed onto the hair may result from the mixing of a composition comprising one or more polymers containing a silicone unit bearing alkoxy-(aminomethyl)-silyl functional groups, preferably of formula (I), and one or more nonionic fixing polymers and/or one or more anionic fixing polymers, and of a composition comprising one or more catalysts as defined previously.

According to another embodiment, the application may be performed in two stages: in a step (A) the composition comprising one or more catalysts as defined previously is applied, in a step (B) the composition comprising one or more polymers containing a silicone unit bearing alkoxy-(aminomethyl)-silyl functional groups, preferably of formula (I), and one or more nonionic fixing polymers and/or one or more anionic fixing polymers is applied by spraying. In this embodiment, step (A) may be performed, followed by step (B), or alternatively step (B) may be performed, followed by step (A), with or without intermediate drying. Preferably, step (A) is performed, followed by step (B). In this particular embodiment, intermediate drying is preferably performed.

The invention is illustrated in greater detail in the examples that follow, which are given as non-limiting illustrations of the invention.

EXAMPLE

The following compositions according to the invention were prepared from the ingredients indicated in the tables below, in grams of active material:

|  | 1 | 2 | 3 | 4 |
|---|---|---|---|---|
| Polymer Ic (MW = 13 100) | 4.0 | 4.0 | 2.2 | 2.2 |
| Polyvinylpyrrolidone[1] | 8.0 | — | 4.4 | — |
| Vinylpyrrolidone/vinyl acetate copolymer[2] | — | 8.0 | — | 4.4 |
| Dimethyl ether | — | — | 45 | 45 |
| Isopropanol | qs 100 | qs 100 | qs 100 | qs 100 |

[1]Sold under the trade name Luviskol ® K30 by BASF
[2]Sold under the trade name Luviskol ® VA64 by BASF

|  | 5 | 6 | 7 | 8 | 9 |
|---|---|---|---|---|---|
| Polymer Ic (MW = 13 100) | 4.0 | 4.0 | 4.0 | 4.0 | 4.0 |
| Vinyl acetate/crotonic acid/vinyl neodecanoate terpolymer[3] | 8.0 | 8.0 | — | — | — |
| Acrylic acid/ethyl acetate/N-tert-butylacrylamide terpolymer[4] | — | — | 8.0 | — | — |
| Vinyl acetate/crotonic acid copolymer[5] | — | — | — | 8.0 | — |
| Polydimethyl/methylsiloxane containing methyl 3-thiopropylacrylate/methyl methacrylate/methacrylic acid groups[6] | — | — | — | — | 8.0 |
| Aminomethylpropanol | — | 0.9 | — | — | — |
| Isopropanol | qs 100 | qs 100 | qs 100 | qs 100 | qs 100 |

[3]Sold under the trade name Resyn 28-2930 ® by AkzoNobel
[4]Sold under the trade name Ultrahold Strong ® by BASF
[5]Sold under the trade name Luviset CA66 ® by BASF
[6]Sold under the trade name LO-21 by 3M

|  | 10 | 11 | 12 | 13 | 14 |
|---|---|---|---|---|---|
| Polymer Ic (MW = 13 100) | 2.2 | 2.2 | 2.2 | 2.2 | 2.2 |
| Vinyl acetate/crotonic acid/vinyl neodecanoate terpolymer[3] | 4.4 | 4.4 | — | — | — |
| Acrylic acid/ethyl acetate/N-tert-butylacrylamide terpolymer[4] | — | — | 4.4 | — | — |
| Vinyl acetate/crotonic acid copolymer[5] | — | — | — | 4.4 | — |
| Polydimethyl/methylsiloxane containing methyl 3-thiopropylacrylate/methyl methacrylate/methacrylic acid groups[6] | — | — | — | — | 4.4 |
| Dimethyl ether | 45 | 45 | 45 | 45 | 45 |
| Isopropanol | qs 100 | qs 100 | qs 100 | qs 100 | qs 100 |

[3]Sold under the trade name Resyn 28-2930 ® by AkzoNobel
[4]Sold under the trade name Ultrahold Strong ® by BASF
[5]Sold under the trade name Luviset CA66 ® by BASF
[6]Sold under the trade name LO-21 by 3M For each composition 1 to 14, a comparative composition not comprising any polymer was also prepared.

The aerosol compositions 3, 4 and 10 to 14 prepared above and also their respective comparative compositions were introduced into an aerosol dispensing device which has the following characteristics:
- a valve equipped with a nozzle with an orifice 0.41 mm in size and an internal orifice 2.03 mm in size,
- a diffuser equipped with a turbulent-channel nozzle whose orifice is 0.38 mm in diameter.

1.5 g of these aerosol compositions were sprayed onto 5.4 g locks of dry hair laid out in a fan shape (spraying on both sides).

A level of fixing with the compositions according to the invention greater than or equal to that obtained with the comparative compositions is obtained. The fixing is also longer-lasting, or equivalent, with the compositions according to the invention than with the comparative compositions. The fixing persistence in wet medium is also improved with the compositions according to the invention relative to the comparative compositions.

Moreover, a much smoother feel of the hair is obtained from the start of drying of the compositions according to the invention, and even more so after drying.

The invention claimed is:

1. A hair composition comprising
   (i) at least one polymer containing a silicone unit bearing alkoxy-(aminomethyl)-silyl functional groups chosen from compounds according to formula (I) below

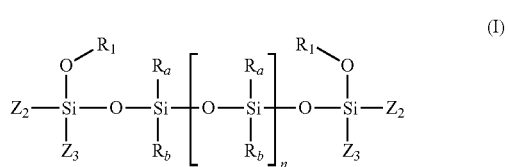

wherein,
   $Z_2$ is chosen from —$CH_2$—$NR_3R_4$ groups;
   $Z_3$ is chosen from $OR_5$ or $R_6$ groups;
   $R_1$ is chosen from $C_1$-$C_6$ alkyl groups;
   $R_3$ is chosen from a hydrogen atom or a $R_7$ group and $R_4$ is chosen from $C_1$-$C_6$ alkyl groups or $C_5$-$C_6$ cycloalkyl groups, or $R_3$ and $R_4$ optionally form, with the nitrogen atom that bears them, a 5- to 8-membered heterocycle comprising from 1 to 3 heteroatoms;

$R_5$, $R_6$, and $R_7$, which may be identical or different, are chosen from $C_1$-$C_6$ alkyl groups;

$R_a$ and $R_b$ which may be identical or different, are chosen from $C_1$-$C_2$ alkyl groups; and n is an integer greater than 1; and (ii) at least one nonionic fixing polymer and/or anionic fixing polymer.

2. The composition according to claim 1, wherein the $C_1$-$C_6$ alkyl groups are chosen from methyl or ethyl groups.

3. The composition according to claim 1, wherein $R_3$ and $R_4$ form, with the nitrogen atom that bears them, a 5- to 8-membered heterocycle comprising from 1 to 3 heteroatoms.

4. The composition according to claim 3, wherein $R_3$ and $R_4$ form, with the nitrogen atom that bears them, a cyclic group, and $R_5$ is an ethyl group.

5. The composition according to claim 1, wherein n is an integer ranging from 1 to 10,000.

6. The composition according to claim 1, wherein $SiR_aR_b$—$[OSiR_aR_b]n$- of formula (I) is a unit derived from a linear silicone with a weight-average molecular mass (Mw) ranging from about 200 g/mol to about 40,000 g/mol.

7. The composition according to claim 1, wherein the at least one polymer containing a silicone unit bearing alkoxy-(aminomethyl)-silyl functional groups is present in an amount ranging from about 0.1% to about 40% by weight, relative to the total weight of the composition.

8. The composition according to claim 1, wherein the at least one anionic fixing polymer is chosen from acrylic or methacrylic acid copolymers or salts thereof, crotonic acid copolymers, polyacrylamides bearing carboxylate groups, homopolymers or copolymers bearing sulfonic groups, anionic polyurethanes, or anionic grafted silicone polymers.

9. The composition according to claim 1, wherein the at least one nonionic fixing polymer is chosen from polyalkyloxazolines, vinyl acetate homopolymers, vinyl acetate copolymers, acrylic ester homopolymers and copolymers, copolymers of acrylonitrile and of a nonionic monomer, styrene homopolymers, styrene copolymers, polyamides, vinyllactam homopolymers, vinyllactam copolymers, or polyvinyl alcohols.

10. The composition according to claim 1, wherein the at least one nonionic fixing polymer and/or anionic fixing polymer is present in an amount ranging from about 0.1% to about 20% by weight, relative to the total weight of the composition.

11. The composition according to claim 1, further comprising at least one organic solvent chosen from alcohols, alkanes, esters, silicones, or mixtures thereof.

12. The composition according to claim 11, wherein the at least one organic solvent is present in an amount ranging from about 10% to about 99.8% by weight, relative to the total weight of the composition.

13. The composition according to claim 1, further comprising water in amount less than about 5% by weight, relative to the total weight of the composition.

14. The composition according to claim 1, further comprising at least one catalyst chosen from organic or mineral basic compounds, organic or mineral acids, or mixtures thereof.

15. The composition according to claim 14, wherein the at least one catalyst is present in an amount ranging from about 0.0001% to about 10% by weight, relative to the total weight of the composition.

16. An aerosol device comprising a container comprising a composition, the composition comprising:

(i) at least one polymer containing a silicone unit bearing alkoxy-(aminomethyl)-silyl functional groups chosen from compounds according to formula (I) below $$Z_2-\underset{\underset{Z_3}{|}}{\overset{\overset{O\diagup R_1}{|}}{Si}}-O-\underset{\underset{R_b}{|}}{\overset{\overset{R_a}{|}}{Si}}-\left[O-\underset{\underset{R_b}{|}}{\overset{\overset{R_a}{|}}{Si}}\right]_n-O-\underset{\underset{Z_3}{|}}{\overset{\overset{R_1\diagdown O}{|}}{Si}}-Z_2 \quad (I)$$

wherein, $Z_2$ is chosen from —$CH_2$—$NR_3R_4$ groups;

$Z_3$ is chosen from $OR_5$ or $R_6$ groups;

$R_1$ is chosen from $C_1$-$C_6$ alkyl groups;

$R_3$ is chosen from a hydrogen atom or a $R_7$ group and $R_4$ is chosen from $C_1$-$C_6$ alkyl groups or $C_5$-$C_6$ cycloalkyl groups, or $R_3$ and $R_4$ optionally form, with the nitrogen atom that bears them, a 5- to 8-membered heterocycle comprising from 1 to 3 heteroatoms;

$R_5$, $R_6$, and $R_7$, which may be identical or different, are chosen from $C_1$-$C_6$ alkyl groups;

$R_a$ and $R_b$ which may be identical or different, are chosen from $C_1$-$C_2$ alkyl groups; and n is an integer greater than 1, and (ii) at least one nonionic fixing polymer and/or anionic fixing polymer; and at least one propellant gas.

17. The device according to claim 16, wherein the at least one propellant is chosen from compressed air, nitrogen, carbon dioxide, dimethyl ether, volatile hydrocarbons, chlorinated and/or fluorinated hydrocarbons, or mixtures thereof.

18. The device according to claim 16, wherein the at least one propellant is present in the composition in an amount ranging from about 2% to about 90% by weight, relative to the total weight of the composition.

19. A method for shaping and/or holding hair, comprising applying to the hair a composition comprising:

(i) at least one polymer containing a silicone unit bearing alkoxy-(aminomethyl)-silyl functional groups chosen from compounds according to formula (I) below $$Z_2-\underset{\underset{Z_3}{|}}{\overset{\overset{O\diagup R_1}{|}}{Si}}-O-\underset{\underset{R_b}{|}}{\overset{\overset{R_a}{|}}{Si}}-\left[O-\underset{\underset{R_b}{|}}{\overset{\overset{R_a}{|}}{Si}}\right]_n-O-\underset{\underset{Z_3}{|}}{\overset{\overset{R_1\diagdown O}{|}}{Si}}-Z_2 \quad (I)$$

wherein, $Z_2$ is chosen from —$CH_2$—$NR_3R_4$ groups;

$Z_3$ is chosen from $OR_5$ or $R_6$ groups;

$R_1$ is chosen from $C_1$-$C_6$ alkyl groups;

$R_3$ is chosen from a hydrogen atom or a $R_7$ group and $R_4$ is chosen from $C_1$-$C_6$ alkyl groups or $C_5$-$C_6$ cycloalkyl groups, or $R_3$ and $R_4$ optionally form, with the nitrogen atom that bears them, a 5- to 8-membered heterocycle comprising from 1 to 3 heteroatoms;

$R_5$, $R_6$, and $R_7$, which may be Identical or different, are chosen from $C_1$-$C_6$ alkyl groups;

$R_a$ and $R_b$ which may be identical or different are chosen from $C_1$-$C_2$ alkyl groups; and n is an integer greater than 1, and (ii) at least one nonionic fixing polymer and/or anionic fixing polymer.

* * * * *